US011322010B1

(12) United States Patent
Madden et al.

(10) Patent No.: US 11,322,010 B1
(45) Date of Patent: *May 3, 2022

(54) SWIMMING POOL MONITORING

(71) Applicant: Alarm.com Incorporated, Tysons, VA (US)

(72) Inventors: Donald Madden, Columbia, MD (US); Daniel Todd Kerzner, McLean, VA (US)

(73) Assignee: Alarm.com Incorporated, Tysons, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,548

(22) Filed: Jan. 17, 2020

Related U.S. Application Data

(60) Provisional application No. 62/793,568, filed on Jan. 17, 2019.

(51) Int. Cl.

| H04N 7/18 | (2006.01) |
|---|---|
| G08B 21/08 | (2006.01) |
| G01S 15/86 | (2020.01) |
| G06N 3/08 | (2006.01) |
| G06N 3/04 | (2006.01) |
| G06K 9/62 | (2022.01) |
| G06V 20/52 | (2022.01) |
| G06V 40/10 | (2022.01) |
| G06V 40/20 | (2022.01) |
| G01N 33/18 | (2006.01) |

(52) U.S. Cl.
CPC ............ *G08B 21/084* (2013.01); *G01S 15/86* (2020.01); *G06K 9/6217* (2013.01); *G06N 3/04* (2013.01); *G06N 3/08* (2013.01); *G06V 20/52* (2022.01); *G06V 40/10* (2022.01); *G06V 40/20* (2022.01); *H04N 7/181* (2013.01); *H04N 7/188* (2013.01); *G01N 33/18* (2013.01)

(58) Field of Classification Search
CPC ............ G08B 21/084; G06K 9/00771; G06K 9/00335; G06K 9/6217; G06K 9/00362; H04N 7/188; H04N 7/181; G06N 3/08; G06N 3/04; G01S 15/86; G01N 33/18
USPC .......................................................... 348/81
See application file for complete search history.

(56) References Cited

U.S. PATENT DOCUMENTS

| 8,669,876 B2 | 3/2014 | Anderson et al. |
|---|---|---|
| 9,049,352 B2 | 6/2015 | Scalisi et al. |

(Continued)

OTHER PUBLICATIONS

Alshbatat et al., Automated vision bases surveillance system to detect drowning incidents in swimming pools (Year: 2020).*

(Continued)

*Primary Examiner* — Shan E Elahi
(74) *Attorney, Agent, or Firm* — Fish & Richardson P.C.

(57) ABSTRACT

A monitor control unit that is configured to receive, from the electronic pool device, the sensor data, compare the sensor data to a threshold, based on comparing the sensor data to a threshold, determine that the sensor data exceeds the threshold, based on determining that the sensor data exceeds the threshold, provide an instruction to initiate the capture of image data by the camera of the electronic pool device, receive, from the camera of the electronic pool device, the image data, analyze the image data, based on analyzing the image data, identify a monitoring system action to perform, and perform the monitoring system action.

20 Claims, 9 Drawing Sheets

(56) References Cited

U.S. PATENT DOCUMENTS

| | | | |
|---|---|---|---|
| 9,668,041 B2 | 5/2017 | Vavrus et al. | |
| 9,940,826 B1* | 4/2018 | Divakara | G08B 29/183 |
| 10,665,073 B1* | 5/2020 | Richerson, Jr. | G03B 17/08 |
| 10,825,319 B1* | 11/2020 | Madden | H04N 7/185 |
| 2005/0167345 A1* | 8/2005 | De Wet | C02F 1/008 |
| | | | 210/85 |
| 2008/0106422 A1* | 5/2008 | Sparks | E04H 4/14 |
| | | | 340/573.6 |
| 2008/0311898 A1* | 12/2008 | Benco | G08B 21/08 |
| | | | 455/419 |
| 2010/0169220 A1* | 7/2010 | Choing | G06Q 40/08 |
| | | | 705/51 |
| 2010/0304934 A1* | 12/2010 | Woodson | A63B 24/0062 |
| | | | 482/8 |
| 2014/0266684 A1* | 9/2014 | Poder | G08B 25/001 |
| | | | 340/521 |
| 2014/0303757 A1* | 10/2014 | Pruchniewski | H04L 61/20 |
| | | | 700/90 |
| 2015/0092055 A1* | 4/2015 | Scalisi | G08B 21/088 |
| | | | 348/143 |
| 2015/0112885 A1* | 4/2015 | Fadell | G08B 25/008 |
| | | | 705/330 |
| 2015/0226805 A1* | 8/2015 | Albers | H04Q 9/00 |
| | | | 702/182 |
| 2016/0044287 A1 | 2/2016 | Scalisi et al. | |
| 2016/0104359 A1* | 4/2016 | AlMahmoud | G01S 15/42 |
| | | | 367/112 |
| 2017/0223314 A1* | 8/2017 | Collings, III | G01S 5/20 |
| 2017/0365150 A1* | 12/2017 | Bennett | G06N 20/00 |
| 2018/0000346 A1* | 1/2018 | Cronin | A61B 5/6801 |
| 2018/0031266 A1* | 2/2018 | Atchison | F24F 11/30 |
| 2018/0089980 A1* | 3/2018 | Snyder | G06K 9/00771 |
| 2018/0112430 A1* | 4/2018 | Shalon | C02F 1/685 |
| 2018/0342329 A1* | 11/2018 | Rufo | H04L 12/2812 |
| 2019/0045207 A1* | 2/2019 | Chen | G06K 9/4628 |
| 2019/0287378 A1* | 9/2019 | Rogers | G01S 15/86 |

OTHER PUBLICATIONS

Xiao et al, Research and design of Zigbee based swimming pool positioning anti-flooding device (Year: 2018).*

* cited by examiner

SWIMMING POOL MONITORING

CROSS REFERENCE TO RELATED APPLICATION

This application claims benefit of U.S. Provisional Application No. 62/793,568 filed Jan. 17, 2019, and titled "Swimming Pool Monitoring," which is incorporated by reference in its entirety.

TECHNICAL FIELD

This disclosure relates to property monitoring technology and, for example, using video analytics and other techniques to monitor the activity at a swimming pool.

BACKGROUND

Many people equip homes and businesses with monitoring systems to provide increased security for their homes and businesses.

SUMMARY

Techniques are described for monitoring technology. For example, techniques are described for using video analytics and other techniques to monitor the area around a swimming pool for prohibited activity.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DETAILED DESCRIPTION

Pool safety is important regardless of whether a homeowner is at the residence or the residence is vacant. Over the past ten years, there has been an average of over three thousand fatal drownings per year. Many of these drownings were the result of an unattended pool.

Techniques are described for integrating an electronic pool device into a monitoring system to facilitate the monitoring of a swimming pool at a monitored property. The electronic pool device may include a battery powered camera and one or more sensors configured to detect motion in the swimming pool. The electronic pool device may be in communication with a control unit of the monitoring system at the monitored property. The electronic pool device monitors for unexpected activity at the pool. For example, the electronic pool device generates an alert to a user when motion is detected at the pool while the pool is not in use.

In addition, techniques are described for using video analytics to detect when person(s) are performing prohibited activities around the swimming pool. One or more cameras that are time synchronized and spatially calibrated which each other, may be fixed around the swimming pool and may be used to monitor the pool and the surrounding pool side areas for persons performing prohibited actions. For example, the one or more cameras may monitor the area around the pool for persons that are running around the swimming pool. The one or more cameras that are time synchronized and spatially calibrated with each other allows the system to track a person as the person moves through the monitored area and video data of the person is captured by the one or more cameras.

Figure 1:
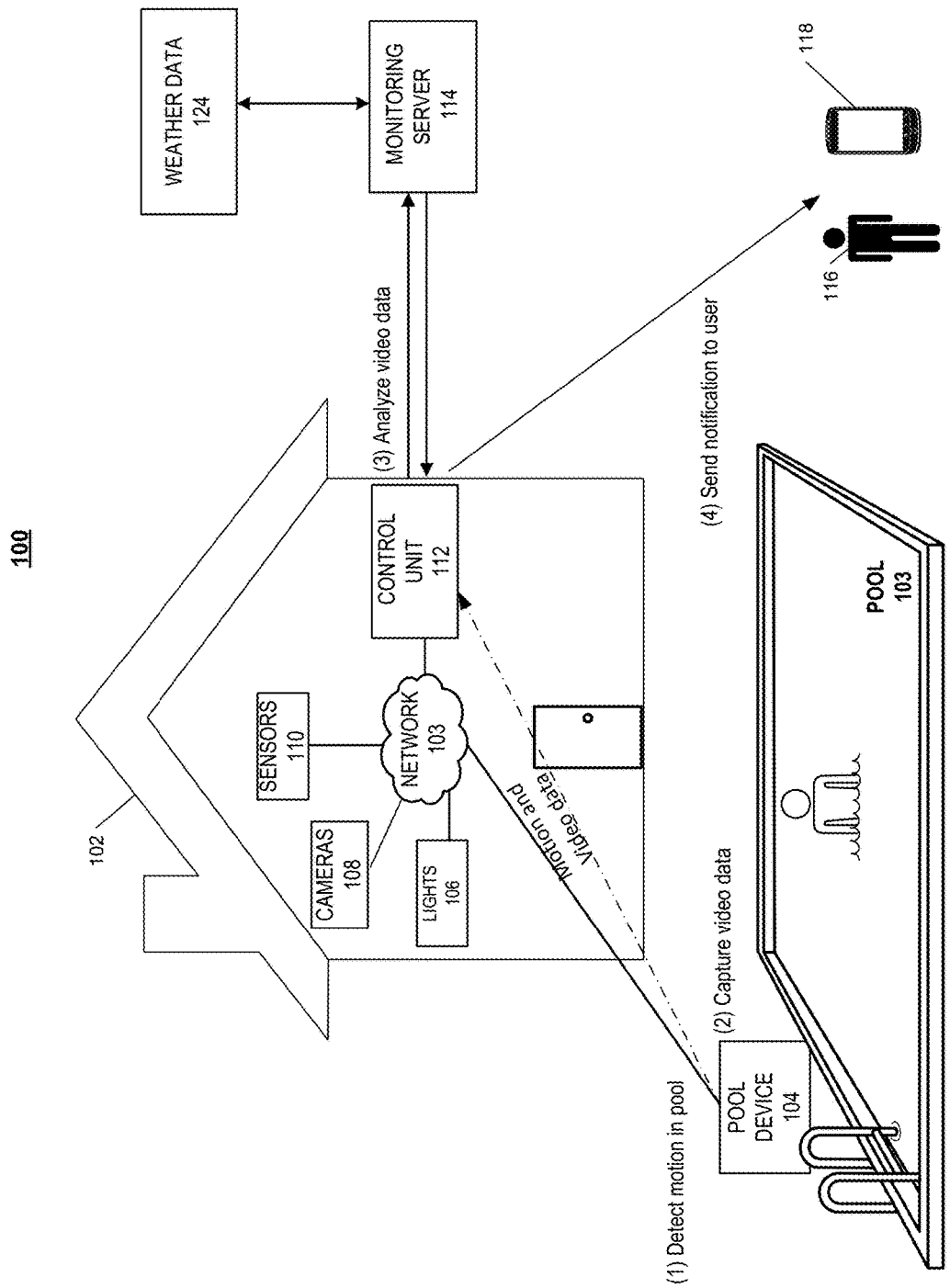
FIG. 1 illustrates an example of a system for detecting motion in a swimming pool.

FIG. 1 illustrates an example of a monitoring system 100 integrated with an electronic pool device. As shown in FIG. 1, a property 102 (e.g. a home) of a user 116 is monitored by an in-home monitoring system (e.g. in-home security system) that includes components that are fixed within the property 102. The in-home monitoring system may include a control unit 112, one or more sensors 110, one or more cameras 108, one or more lights 106, and an electronic pool device 104. Each of the one or more sensors 110, one or more cameras 108, one or more lights 106, and the electronic pool device 104 are in communication with the control unit 112 to form the monitoring ecosystem of the monitored property.

The user may integrate the electronic pool device 104 to monitor the conditions of a swimming pool 103 at the monitored property 102. The swimming pool 103 may be an indoor pool located within the monitored property 102, or an outdoor pool located on the lawn of the monitored property 102. In some examples, the electronic pool device 104 may be used to monitor the conditions of a hot tub. In these examples, the electronic pool device 104 may be configured to detect only motion not caused by the bubbles generated in the hot tub. The electronic pool device 104 also monitors the pool for unexpected movement, for example when a child slips into the pool 103. The electronic pool device 104 may be used to monitor the pool water temperature, the pool water pH levels, and any other suitable status conditions.

The electronic pool device 104 may include a camera portion that is configured to be placed under the surface of the water, and a surface portion that includes an antenna, a microphone and one or more motion detecting sensors. The one or more motion detecting sensors may include an accelerometer, a gyroscope, a mercury switch, or any other appropriate motion detecting sensors. The camera portion and the surface portion of the electronic pool device 104 may each be waterproof. The antenna is configured to allow the electronic pool device 104 to communicate with the control unit 112. In some implementations, the electronic pool device 104 may communicate with the control unit 112 through Bluetooth, Z-Wave, ZigBee, Wi-Fi, or other suitable form of wireless communication.

The camera portion of the electronic pool device 104 includes a rechargeable battery that is charged by the energy generated from the water flowing through the pool's plumbing system. The camera portion of the electronic pool device 104 may be configured to mount to an existing pool jet, and the battery of the camera portion charges as water flows through the pool jet. In some implementations, the camera portion of the electronic pool device 104 may be in communication with a distinct fitting that is mounted to the pool jet or is in communication with a skimmer, or an irrigation system. As the pool water flows through the fitting or the skimmer, the energy generated is transferred to the battery. In some implementations, the camera portion of the electronic pool device 104 may be charged through a solar panel located on the surface portion of the device 104. The camera portion of the electronic pool device 104 is connected to the surface portion of the device by a flexible tether. The tether may be configured to allow the surface portion of the device 104 to float on the surface of the water immediately above the camera portion.

For the example illustrated in FIG. 1, the electronic pool device 104 detects motion in the pool. In some implementations, the electronic pool device 104 is placed in the swimming pool 103 when the pool is not being utilized. In these implementations, when the one or more motion sensors of the surface portion of electronic pool device 104 detect motion in the pool, the motion is considered as unexpected motion, and may trigger an alarm or some other form of notification to be generated. For example, the electronic pool device 104 may be placed in the pool 103 when an adult user does not expect any users in the pool 103.

The one or more motion sensors of the surface portion of the electronic device 104 communicate the motion data to the control unit 112. The control unit 112 compares the motion data to a motion threshold. The motion threshold may be a threshold determined by the control unit 112 based on the weather conditions at the location of the monitored property 102. The control unit 112 at the monitored property 102 may receive weather data from a weather data server 124. In some examples, the weather data server 124 is in direct communication with the control unit 112. In other examples, the weather data server 124 communicates with a monitoring server 114 which in turn communicates with the control unit 112. The control unit 112 may adjust the motion threshold based on the weather data indicating windy or rainy conditions.

The control unit 112 may adjust the motion threshold based on the time of the day. For example, the control unit may increase the motion threshold during the weekday between the hours of 8:00 am and 3:00 pm when the residents of the property 102 are away from the home. In these examples, the control unit 112 increases the motion threshold to ensure only motion caused by a person entering the pool triggers an alarm or a notification to be generated. The control unit 112 may decrease the motion threshold during the weekday evening hours and the weekend when the residents of the property 102 are more likely to be at the property. In these examples, the control unit 112 decreases the motion threshold to ensure the any motion detected generates a notification to the resident. The control unit 112 may adjust the motion threshold based on the armed status of the property 102. For example, when the monitoring system at the monitored property 102 is armed away, the system assumes that the residents of the property are away and the control unit increases the motion threshold. For another example, when the monitoring system is armed stay, the system assumes that the residents of the property are at the property and the control unit decreases the motion threshold.

In some implementations, when the motion detected by the one or more motion detection sensors exceeds the motion threshold, the control unit 112 generates a notification. The user 116 may set one or more rules for the types of notifications generated by the control unit 112. The user 116 may log into a monitoring system application that runs on the user device 118 and that is managed by the control unit 112. For example, the user may set preferences to receive a notification on the user device 118 when the pool device 104 detects motion. The user may configure their preferences to receive one or more different notifications based on one or more different thresholds. For example, the user may set their preferences to receive a notification when a first motion threshold is exceeded, and the user may set their preferences to generate an alarm when a second motion threshold is exceeded. In another example, the user 116 may set preferences to generate an alarm at the monitored property 102 when the pool device 104 detects motion.

In another example, the user 116 may set preferences to activate one or more lights in the vicinity of the pool 103 when the pool device detects motion during a specific time of the day. For example, the user may set their preferences to activate one or more lights in the vicinity of the pool 103 when the pool device 104 detects motion after 6:00 PM. In some implementations, the monitoring server 114 manages the monitoring system application. In some examples, when the electronic pool device 104 detects movement after a specific time, the control unit 112 prompts a speaker on the surface portion of the device to generate an audible alert. For example, when the device 104 detects motion after 6:00 PM, the control unit 112 generates an audible alert.

The electronic pool device 104 may also include a pH monitor, and one or more thermometers that monitor the pool conditions. The pH monitor may be located on an under surface of the surface portion of the device 104, and is configured to measure the pH of the pool water. In some examples, the pH monitor may be located on the camera portion of the electronic device 104. The user 116 may set one or more preferences for receiving notifications from the control unit 112 based on the measured pH readings. For example, the user 116 may set a preference to receive a notification when the pH exceeds a threshold value. The camera portion of the electronic device 104 includes a thermometer that measures the temperature of the pool water, and the surface portion of the device 104 includes a thermometer that measures the air temperature. The user 116 may set one or more preferences for receiving notifications from the control unit 112 based on the measured temperatures.

The electronic pool device 104 may monitor one or more other pool conditions. For example, the camera of the device 104 may detect debris at the bottom of the pool, and based on detecting the debris at the bottom of the pool, the control unit 112 communicates a notification to the user 116 indicating that maintenance is required. For another example, the camera of the device 104 may detect that the pool water is cloudy, and based on detecting the pool water is cloudy, the control unit 112 communicates a notification to the user 116 indicating that maintenance is required. In some implementations, the control unit 112 may periodically initiate communication with the electronic pool device 104. In the event that the electronic pool device 104 fails to respond to the communication initiated by the control unit 112, the control unit 112 may generate an alert to the user notifying the user that the electronic pool device 104 is offline. In some implementations, when the electronic pool device 104 fails to respond to the communication initiated by the control unit 112, the control unit 112 may initiate additional monitoring of the pool area. For example, the one or more cameras that have the pool 103 within their field of view may be powered on, and the captured video data is communicated to and analyzed by the control unit 112.

In other implementations, the electronic pool device 104 remains in the swimming pool 103 at all times. In these implementations, the camera portion of the electronic pool device 104 may include a sonar detector. The sonar detector is configured to detect objects under the surface of the water of the swimming pool 103. During a configuration stage, the sonar detector characterizes the underwater portion of the empty swimming pool 103. The sonar detector emits sound pulses and detects the sound pulses that are reflected off the surfaces of the swimming pool 03, and back to the sonar detector. The sonar detector generates a signature reflection pattern of the swimming pool 103 based on the data collected during configuration. The sonar detector is configured to detect when there is a change in the reflection pattern of the underwater profile of the pool 103, based on the reflection data received at the detector. When the sonar detector receives a reflection pattern that is different than the signature reflection pattern collected during configuration, the sonar detector determines an object entered the swimming pool 103.

The electronic pool device 104 communicates the sonar data to the control unit 112. The control unit 112 may implement one or more algorithms to determine whether the data detected by the sonar detector was caused by an object and not by other factors such as, weather or a vibration from the pool pump. During configuration, the system may be trained to rule out noise patterns that may cause the sonar detector to detect movement. When the control unit 112 determines the sonar data indicates the motion was caused by an object in the swimming pool 103, the control unit 112 generates a notification. The notification may be communicated to the user device 118 of the user 116 as an in-app notification.

In some implementations, the notification may include video data collected by the camera of the electronic pool device 104. When the sonar detector detects an object has entered the swimming pool 103, the camera may automatically begin to capture video data. The camera portion of the electronic device 104 may be positioned with a 180° field of view. The camera may be positioned so that each side surface of the swimming pool 103 is within the field of view of the camera. In some implementations, the swimming pool 103 may include one or more underwater cameras that are in communication with each other and in communication with the electronic pool device 104. The electronic pool device 104 may communicate the captured video data to the user device 118 of the user 116. The user 116 may review the captured data to determine whether the motion was caused by a person or pet in the pool 103, or whether the motion was caused by an object.

The user may indicate, through the monitoring system application, whether the motion was caused by a person or was caused by an object. For example, the user may review the video data and select a response indicating that the motion was caused by an object. The control unit 112 does not generate an alarm based on receiving data from the user 116 indicating the motion was caused by an object. The control unit may update the one or more motion thresholds based on the data received from the user indicating the motion was caused by an object.

When the user reviews the video data and selects a response indicating that the motion was by a person, the control unit 112 may generate an audible alarm at the monitoring property 102. The control unit 112 may communicate with an external server to dispatch authorities to the property 102 based on determining the user device 118 of the user is outside of a threshold distance from the property 102. For example, the control unit 112 may communicate directly with authority dispatch server. In other examples the control unit 112 communicates with the monitoring server 114 which in turn communicates with the authority dispatch server.

In some implementations, the surface portion of the electronic pool device 104 may include a switch that allows the user 116 to switch on the camera of the device 104. In these implementations, the user 116 may switch on the camera of the device 104 when the pool 103 is being utilized. When the pool 103 is being utilized the video data collected by the camera may be communicated to the control unit 112. The control unit 112 may be trained to identify data indicative of a swimmer in distress. During configuration of the electronic pool device 104, the control unit 112 may receive labeled data sets that teach the camera to identify a distressed swimmer. The user 116 may provide true or false responses based on reviewing video data of different actions in the captured video data. The user 116 may review the video data and the determinations made by the control unit 112 to respond whether each of the determinations was true or false. For example, the system may determine a person is swimming in the pool 103, and the user may confirm whether the person was swimming or was in distress.

In some implementations, when the in-home monitoring system is armed away, the control unit 112 assumes that the occupants of the monitored property 102 are away. The control unit 112 may confirm whether the property 102 is unoccupied by using one or more electronic devices and sensors located throughout the property 102. For example, the control unit 112 may switch on one or more cameras to scan the one or more rooms of the property to ensure the property is unoccupied. The control unit 112 may contact the authorities in response to detecting motion in the swimming pool of the monitored property 102. The control unit 112 may contact the authorities when the motion detected in the swimming pool exceeds a high motion threshold. The control unit may determine to contact the police department when the high motion threshold is exceeded when the homeowners are away from the property 102. In some implementations, when the high motion threshold is exceeded and the homeowners are away from the property 102, the control unit 112 may prompt the one or more cameras in the pool 103 vicinity to capture video data. The control unit 112 may use one or more video analytic techniques to determine whether the motion is caused by a human or an object. In some implementations, the control unit may be configured to perform facial recognition on the video data to identify the person detected in the swimming pool 103. In these implementations, the control unit 112 may generate one or more different notifications based on the identity of the person.

In some implementations, the swimming pool may be located at a property that is not monitored by a monitoring system. In these implementations, the pool device may communicate with an external monitoring server via cellular communication. The pool device may monitor for motion and communicate detected motion to the monitoring server.

Figure 2:
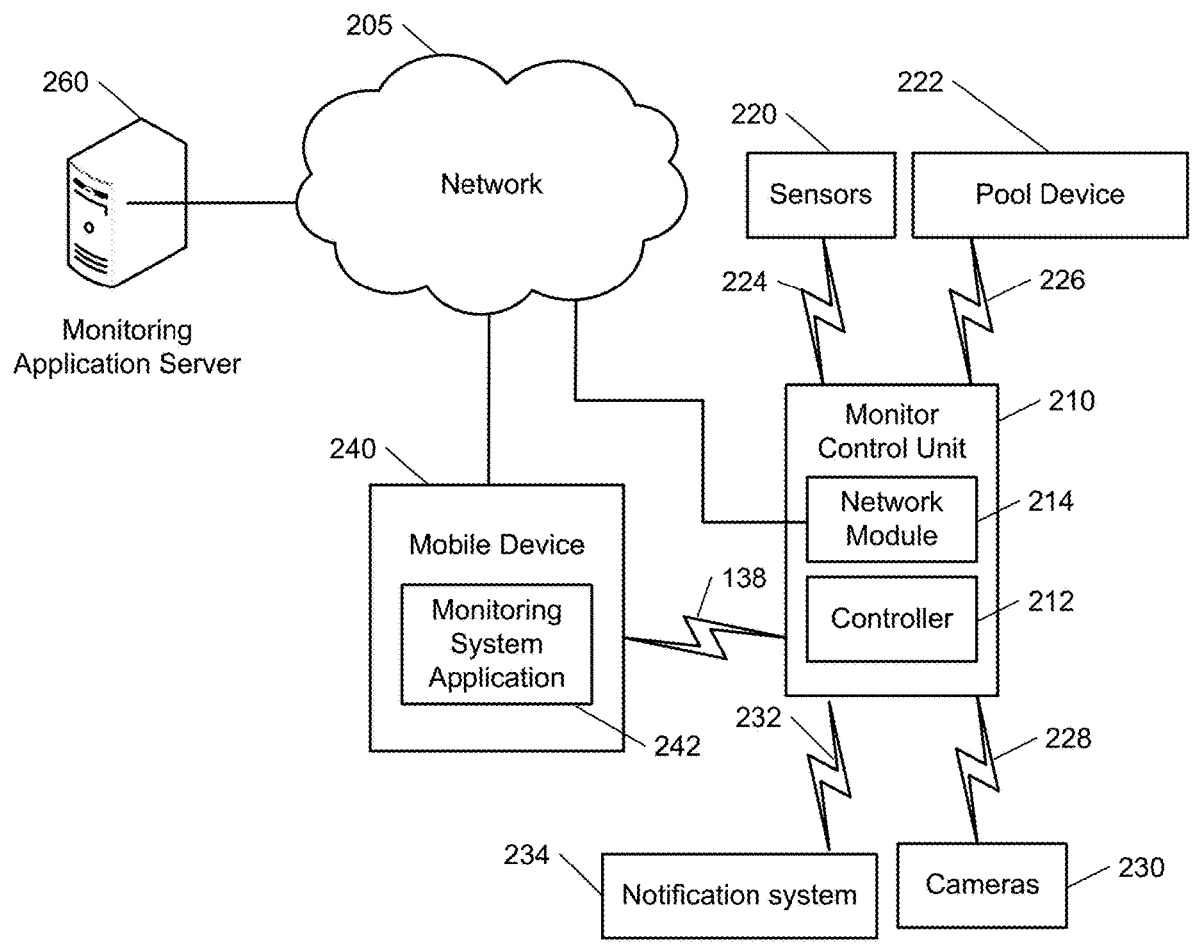
FIG. 2 illustrates an example of a monitoring system integrated with an electronic pool device.

FIG. 2 illustrates an example of a system 200 configured to monitor a property. The system 200 includes a network 205, a monitoring system control unit 210, one or more user devices 240, and a monitoring application server 260. The network 205 facilitates communications between the monitoring system control unit 210, the one or more user devices 240, and the monitoring application server 260. The network 205 is configured to enable exchange of electronic communications between devices connected to the network 205. For example, the network 205 may be configured to enable exchange of electronic communications between the monitoring system control unit 210, the one or more user devices 240, and the monitoring application server 260. The network 205 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. Network 205 may include multiple networks or subnetworks, each of which may include, for example, a wired or wireless data pathway. The network 205 may include a circuit-switched network, a packet-switched data network, or any other network able to carry electronic communications (e.g., data or voice communications). For example, the network 205 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 205 may include one or more networks that include wireless data channels and wireless voice channels. The network 205 may be a wireless network, a broadband network, or a combination of networks including a wireless network and a broadband network.

The monitoring system control unit 210 includes a controller 212 and a network module 214. The controller 212 is configured to control a monitoring system (e.g., a home alarm or security system) that includes the monitor control unit 210. In some examples, the controller 212 may include a processor or other control circuitry configured to execute instructions of a program that controls operation of an alarm system. In these examples, the controller 212 may be configured to receive input from cameras, sensors, detectors, or other devices included in the alarm system and control operations of devices included in the alarm system or other household devices (e.g., a thermostat, an appliance, lights, etc.). For example, the controller 212 may be configured to control operation of the network module 214 included in the monitoring system control unit 210.

The network module 214 is a communication device configured to exchange communications over the network 205. The network module 214 may be a wireless communication module configured to exchange wireless communications over the network 205. For example, the network module 214 may be a wireless communication device configured to exchange communications over a wireless data channel and a wireless voice channel. In this example, the network module 214 may transmit alarm data over a wireless data channel and establish a two-way voice communication session over a wireless voice channel. The wireless communication device may include one or more of a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 214 also may be a wired communication module configured to exchange communications over the network 205 using a wired connection. For instance, the network module 214 may be a modem, a network interface card, or another type of network interface device. The network module 214 may be an Ethernet network card configured to enable the monitoring control unit 210 to communicate over a local area network and/or the Internet. The network module 214 also may be a voiceband modem configured to enable the alarm panel to communicate over the telephone lines of Plain Old Telephone Systems (POTS).

The monitoring system may include an electronic pool device 222 that is configured to monitor the swimming pool at monitored property. The electronic pool device 222 may be configured to communicate with the monitor control unit 210 through Bluetooth, Z-Wave, ZigBee, Wi-Fi, or other suitable form of wireless communication. The electronic pool device 222 may include a rechargeable battery that is powered by the energy generated by the water flowing through the plumbing system of the swimming pool. In some examples, the electronic device 222 may include a solar panel that is used to power the device.

The monitoring system may include multiple sensors 220. The sensors 220 may include a contact sensor, a motion sensor, a glass break sensor, or any other type of sensor included in an alarm system or security system. The sensors 220 also may include an environmental sensor, such as a temperature sensor, a water sensor, a rain sensor, a wind sensor, a light sensor, a smoke detector, a carbon monoxide detector, an air quality sensor, etc. The sensors 220 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, etc. In some examples, the sensors 220 may include a radio-frequency identification (RFID) sensor that identifies a particular article that includes a pre-assigned RFID tag.

The one or more cameras 230 may be a video/photographic camera or other type of optical sensing device configured to capture images. For instance, the one or more cameras 230 may be configured to capture images of an area within a building monitored by the monitor control unit 210. The one or more cameras 230 may be configured to capture single, static images of the area and also video images of the area in which multiple images of the area are captured at a relatively high frequency (e.g., thirty images per second). The one or more cameras 230 may be controlled based on commands received from the monitor control unit 210. The one or more outdoor cameras may be video/photographic cameras that are mounted outside of the monitored property. The one or more outdoor cameras may be arranged to ensure that the entire pool and the area surrounding the swimming pool is within the field of view of at least one of the outdoor cameras. Each of the one or more outdoor cameras may be time synchronized and spatially calibrated with respect to each other.

The sensors 220, the pool device 222, and the cameras 230 communicate with the controller 212 over communication links 224, 226, and 228. The communication links 224, 226, and 228 may be a wired or wireless data pathway configured to transmit signals from the sensors 220, the pool device 222, and the cameras 230 to the controller 212. The communication link 224, 226, and 228 may include a local network, such as, 802.11 "Wi-Fi" wireless Ethernet (e.g., using low-power Wi-Fi chipsets), Z-Wave, Power Over Ethernet (POE), Zigbee, Bluetooth, "HomePlug" or other Powerline networks that operate over AC wiring, and a Category 5 (CAT5) or Category 6 (CAT6) wired Ethernet network.

The monitoring application server 260 is an electronic device configured to provide monitoring services by exchanging electronic communications with the monitor control unit 210, and the one or more user devices 240, over the network 205. For example, the monitoring application server 260 may be configured to monitor events (e.g., alarm events) generated by the monitor control unit 210. In this example, the monitoring application server 260 may exchange electronic communications with the network module 214 included in the monitoring system control unit 210 to receive information regarding events (e.g., alarm events) detected by the monitoring system control unit 210. The monitoring application server 260 also may receive information regarding events (e.g., alarm events) from the one or more user devices 240.

The one or more user devices 240 are devices that host and display user interfaces. The user device 240 may be a cellular phone or a non-cellular locally networked device with a display. The user device 240 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 240 may perform functions unrelated to the monitoring system, such as placing personal telephone calls, playing music, playing video, displaying pictures, browsing the Internet, maintaining an electronic calendar, etc.

The user device 240 includes a monitoring system application 242. The monitoring system application 242 refers to a software/firmware program running on the corresponding mobile device that enables the user interface and features described throughout. The user device 240 may load or install the monitoring system application 242 based on data received over a network or data received from local media. The monitoring system application 242 runs on mobile devices platforms, such as iPhone, iPod touch, Blackberry, Google Android, Windows Mobile, etc. The monitoring system application 242 enables the user device 140 to receive and process image and sensor data from the monitoring system.

In some implementations, the one or more user devices 240 communicate with and receive monitoring system data from the monitor control unit 210 using the communication link 238. For instance, the one or more user devices 240 may communicate with the monitor control unit 210 using various local wireless protocols such as Wi-Fi, Bolt, Lora, Bluetooth, Z-Wave, ZigBee, "HomePlug," or other Power-line networks that operate over AC wiring, or Power over Ethernet (POE), or wired protocols such as Ethernet and USB, to connect the one or more user devices 240 to local security and automation equipment. The one or more user devices 240 may connect locally to the monitoring system and its sensors and other devices. The local connection may improve the speed of status and control communications because communicating through the network 205 with a remote server (e.g., the monitoring application server 260) may be significantly slower.

Although the one or more user devices 240 are shown as communicating with the monitor control unit 210, the one or more user devices 240 may communicate directly with the sensors and other devices controlled by the monitor control unit 210. In some implementations, the one or more user devices 240 replace the monitoring system control unit 210 and perform the functions of the monitoring system control unit 210 for local monitoring and long range/offsite communication.

Figure 3:
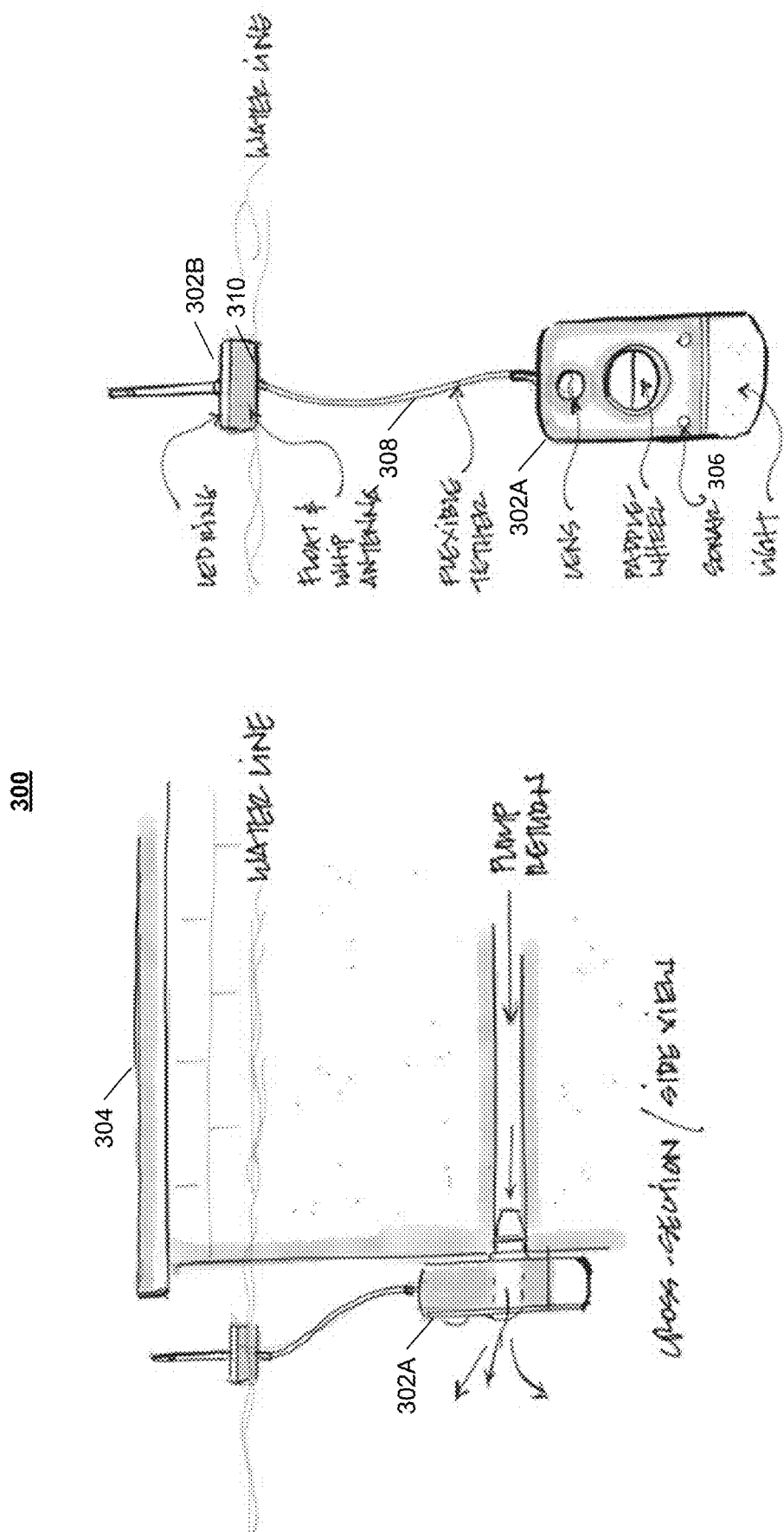
FIG. 3 illustrates an example of an electronic pool device.

FIG. 3 illustrates an example of an electronic pool device. For the implementation illustrated in FIG. 3, the electronic pool device may include a camera portion 302A and a surface portion 302B. The camera portion 302A is configured to be placed under the surface of the water, and may be mounted to an inlet of a pool jet. The pool water that flows through the pool jet may be used to power the battery of the camera portion 302A of the pool device 104. When the battery of the camera portion 302A of the pool device 104 is running low, the pool pump may increase the flow rate of the water through the one or more pool jets to increase the power supplied to the battery. In some implementations, the surface portion 302B may include a solar panel that converts solar energy to power the battery. The surface portion 302B of the electronic pool device is configured to float on the surface of the water of the pool 304. In some implementations, when the pool is in use and a swimmer contacts the surface portion of the pool device 104, the camera initiates the capture of video data.

The surface portion 302B may be attached to the camera portion 302A of the device by a flexible tether 308. In some examples, the tether may be configured to disconnect from the camera portion of the pool device 104 when the tether is under physical stress. The user may receive a notification through the monitoring system application when the control unit receives data from the pool device indicating that the tether disconnected. The surface portion 302B of the device may include an antenna 310 and one or more sensors. The antenna 310 is configured to allow the electronic pool device to communicate with the control unit 112 of the monitored property 102. The surface portion 302B may also include one or more sensors for detecting motion. The one or more motion detecting sensors may include an accelerometer, a gyroscope, a mercury switch, or any other appropriate motion detecting sensors. The surface portion 302B may also include may include a pH sensor, a thermometer, and a microphone.

The microphone on the surface portion 302B of the pool device 104 is a high-sensitivity microphone that is configured to detect an object that causes the pool water to thrash or splash sound when an object enters the pool. When the high-sensitivity microphone detects a splashing sound, the camera may switch on automatically to capture video data. In some implementations, the camera portion 302A of the pool device 104 may include the high sensitivity microphone.

Figure 4A:
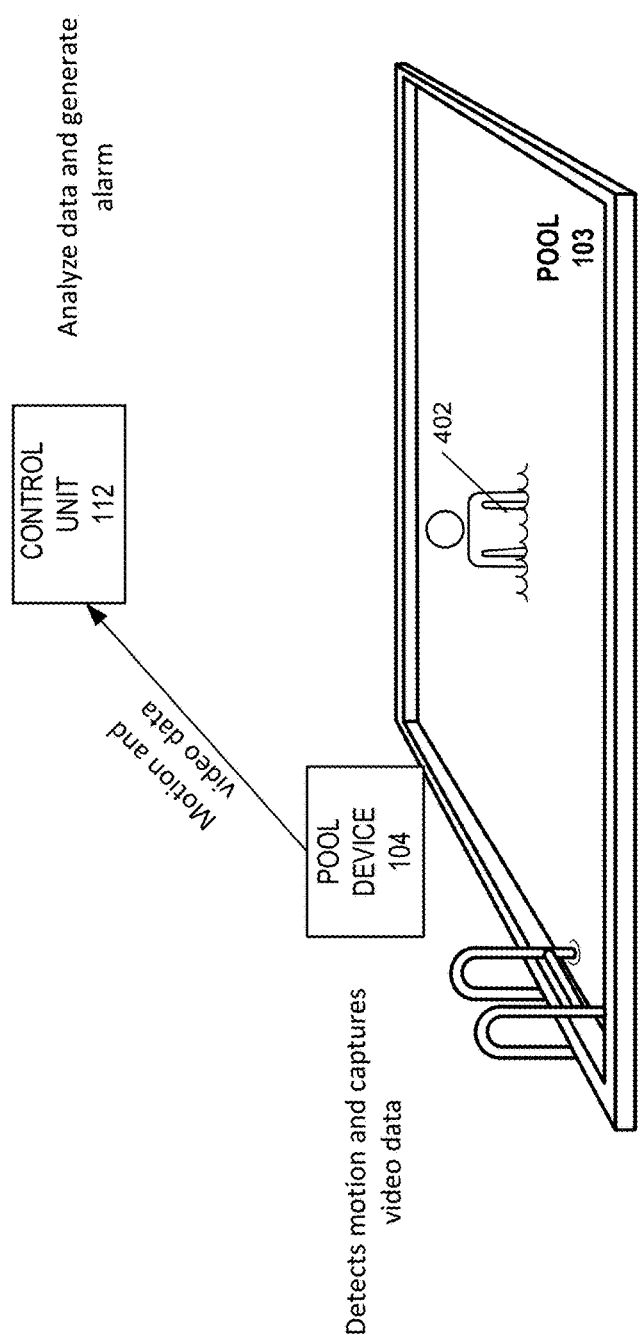
FIGS. 4A and 4B illustrate examples of a system for detecting motion in a swimming pool.
Figure 4B:
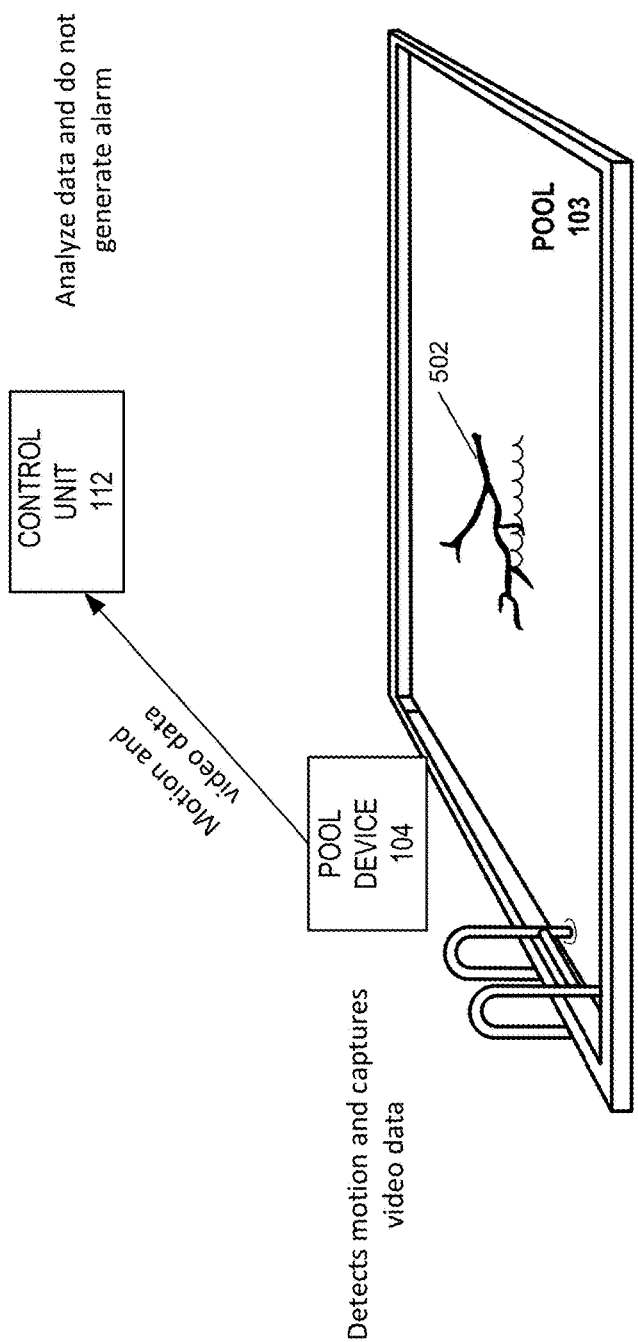

FIGS. 4A and 4B illustrate an example of a system for detecting motion in a swimming pool 103. As illustrated in FIGS. 4A and 4B, the pool device 104 detects motion in the pool 103, and communicates the motion data to the control unit 112. In the implementations where the electronic pool device 104 is placed in the swimming pool 103 when the pool is not being utilized, the one or more motion sensors of the surface portion of the pool device 104 detects motion in the pool 103 and communicates the motion data to the control unit 112. The control unit 112 compares the received motion data to a motion threshold, and based on the motion data exceeding the motion threshold, the control unit 112 communicates a notification to the user device of a resident of the monitored property. The control unit 112 simultaneously commands the camera of the pool device 104 to capture video data.

In the implementations where the electronic pool device 104 remains in the swimming pool 103 at all times, the camera portion of the pool device 104 includes a sonar detector. The sonar detector is configured to detect objects by detecting a change in the reflection pattern of the underwater profile of the swimming pool 103. When the sonar detector receives a reflection pattern that is different than the signature reflection pattern collected during configuration, the sonar detector determines an object entered the swimming pool 103. The pool device 104 communicates the sonar data to the control unit 112, and simultaneously begins to capture video data.

The video data captured by the pool device 104 is communicated to the control unit 112, and the control unit 112 analyzes the video data. The control unit 112 may be configured to use one or more techniques to analyze the video data. The control unit may analyze the data to determine whether the motion was caused by a person or by an object. In some implementations, the control unit may be configured to identify a swimmer in distress.

As illustrated in FIG. 4A, the control unit 112 analyzes the video data and determines that the motion is caused by a user 402. The control unit 112 may send a notification to a user device of a resident of the property, and the notification may include the video data captured by the control unit. The resident of the property may review the video data received. In some implementations, the control unit may be configured to perform facial recognition on the video data to identify the person detected in the swimming pool 103. The user may select an option to have the control unit generate an alarm based on determining that the user 402 in the swimming pool 103 seems to be a trespasser. In some implementations, the control unit 112 may automatically generate an audible alarm at the monitored property based on determining that the user 402 is an unknown user and the monitoring system at the property being armed away.

As illustrated in FIG. 4B, the control unit 112 analyzes the video data and determines that the motion is caused by a tree branch 502. The control unit 112 may send a notification to the user device of the resident of the property indicating that the motion was caused by an object. In these implementations, the control unit 112 does not generate an alarm.

Figure 5:
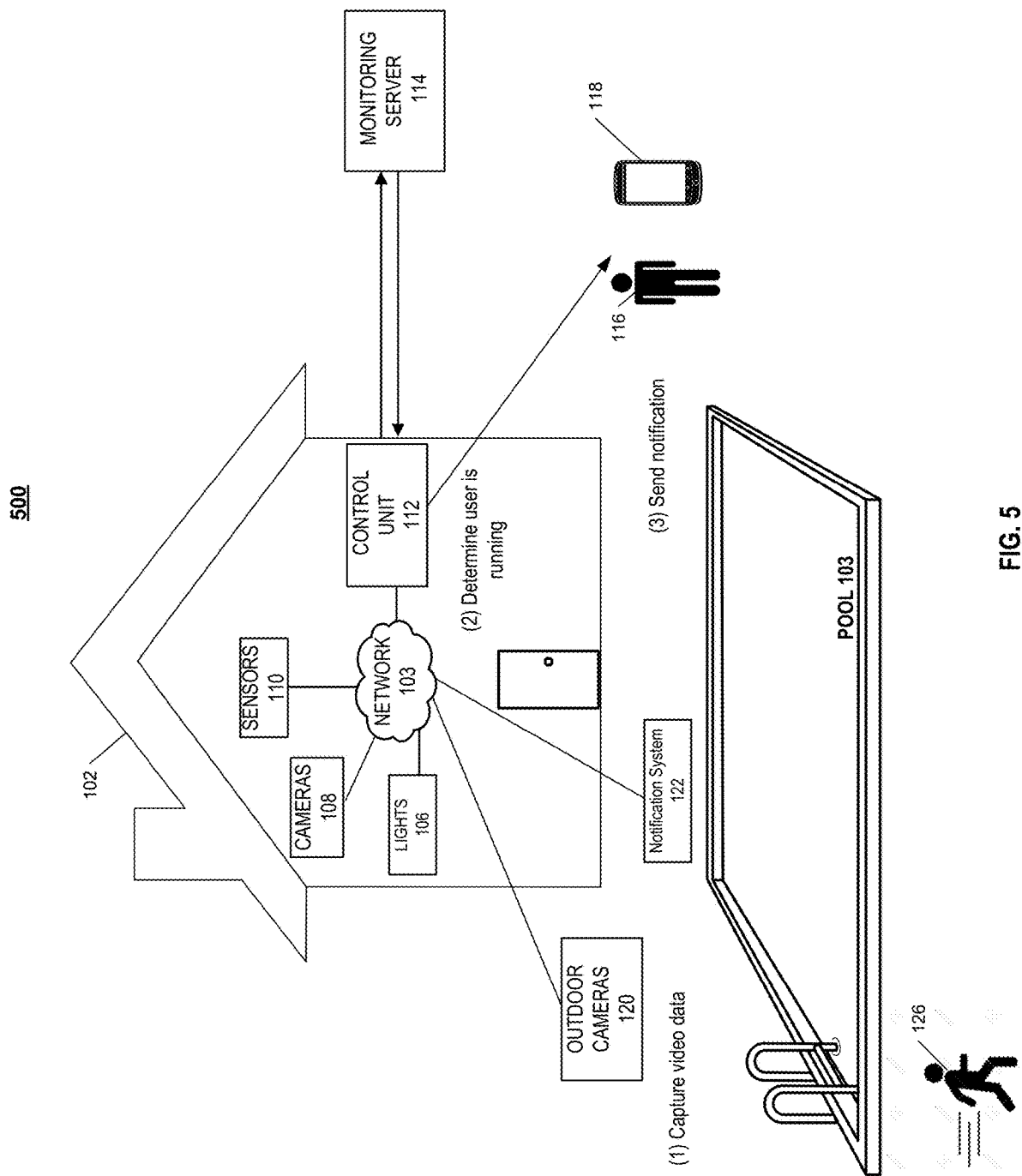
FIG. 5 illustrates an example of a system for detecting a person running in the area around the swimming pool.

FIG. 5 illustrates an example of a monitoring system 500 that includes one or more outdoor cameras 120 that are configured to monitor the activity around the swimming pool 103. As shown in FIG. 5, the property 102 (e.g. a home) of a user 116 is monitored by an in-home monitoring system (e.g. in-home security system) that includes components that are fixed within the property 102. The in-home monitoring system may include a monitor control unit 112, one or more sensors 110, one or more cameras 108, one or more lights 106, one or more outdoor cameras 120, and a notification system 122. In some examples, the in-home monitoring system may also include a pool device 104, for example, as illustrated in FIG. 1.

The user 116 may integrate one or more outdoor cameras 120 to monitor the activity around the swimming pool 103. The one or more outdoor cameras 120 utilize video analytics and other techniques to detect when a user is performing a prohibited action in the area surrounding the swimming pool 103. For example, video analytics may be used to detect when children are present around the pool 103 unsupervised by an adult.

The user 116, a resident of the property 102 may set one or more rules associated with the activity in the area around the swimming pool 103. The user 116 may log into a monitoring application that runs on the user device 118 to set the one or more rules and the applicable one or more zones around the swimming pool 103. The user 116 may have the ability to customize and continuously update the one or more applicable rules. The user 116 may set time schedules for applying the one or more rules. The user 116 may also set the corresponding notification that is generated when a rule is violated by a user. For example, the user 116 may set up rules indicating that no children are allowed around the pool unless accompanied by an adult, and the user may set up a rule that indicates that there should not be any running near the swimming pool. The user 116 may set up one or more different rules for different zones around the swimming pool 103. For example, the user 116 may set up a rule that indicates that diving is not allowed in a first zone at one end of the pool, but diving is allowed in a second zone at the other end of the pool. The user 116 may set up a rule that indicates that eating and drinking is only allowed in a third zone. The notification system 122 may be used to notify a resident or a lifeguard on duty at the swimming pool 103 when the system detects that a user set rule has been violated. For example, a speaker of the notification system may output a whistle sound when a user is detected to be running in the area around the swimming pool 103.

As illustrated in FIG. 5, the one or more outdoor cameras 120 capture video data of the area surrounding the swimming pool 103. The one or more outdoor cameras 120 may be configured to detect when a person moves into the area surrounding the swimming pool 103, and may begin to capture video data when a person is detected. In some implementations, the one or more outdoor cameras 120 may be configured to continuously capture video data. The one or more outdoor cameras 120 may be time-synchronized and spatially calibrated with each other and the spatial dimensions of the swimming pool 103. The one or more cameras 120 may track a user as the user moves around in the area surrounding the swimming pool 103. The one or more cameras may use facial analysis and other techniques to track one or more different users as the one or more users move around in the area surrounding the swimming pool 103. The one or more cameras 120 may use identifiers to tag the one or more users as the users navigate within the monitored area.

The one or more outdoor cameras 120 may communicate the captured video data to a control unit 112. In some implementations, the monitor control unit 112 may include a processing module that is configured to process the video data received from the one or more outdoor cameras 120. In other implementations, each of the one or more outdoor cameras 120 are configured to include a processing module that processes the captured video data. The monitor control unit 112 may use one or more video analytics techniques to detect the activity of the user 126. For example, the monitor control unit 112 utilizes one or more deep learning techniques and or three-dimensional sensing technologies to determine the location of a user with respect to the swimming pool 103, and to determine the activity of the user while in the monitored area.

The monitor control unit 112 may determine the speed of the user 126 detected in the area surrounding the pool 103. For example, the monitor control unit 112 may use machine-learning techniques to analyze the gait of the user 126 to determine whether the user 126 is running. The monitor control unit 112 may determine the speed of the user 126 when the user 126 is determined to be within a monitored area around the pool 103. In some implementations, the monitor control unit 112 determines the speed of each of a one or more users that enter the monitored area around the swimming pool 103, and does not determine the speed of a user until the user enters the monitored area. In some implementations, the monitoring control unit 112 may determine the speed of movement of users based on gauging how fast the user moves from a frame of one camera to a frame of a second camera. Based on the one or more cameras being spatially calibrated, the monitor control unit 112 may determine the user's speed. In some implementations, the monitor control unit 112 may compare the determined speed of the user 126 to a speed threshold to determine whether the user 126 was walking or running. When the user's speed exceeds the speed threshold, the monitor control unit determines that the user 126 is running in the area surrounding the swimming pool 103.

The monitor control unit 112 sends a command to the notification system 122 to generate a notification based on determining that the user 126 violated the no running rule. The notification system 122 may be an electronic notification board that is located outdoor near the swimming pool 103. The notification system 122 may be used to provide audible and visual notifications to a resident user 116 at the property 102. As illustrated in FIG. 5, a speaker of the notification system 122 outputs an automated whistle sound, that simulates a lifeguard's whistle, to notify the user 126 to stop running. The resident 116 may configure the notification system to generate one or more different notifications based on the rule that is violated. For example, the notification system may generate a voice command based on detecting a user eating in a prohibited area near the pool 103. In another example, the notification system may generate an audible alarm based on determining that a child is in the area of the pool 103 without an adult. The notifications generated by the notification system may be different based on the severity of the violation. In the example illustrated in FIG. 5, the monitor control unit 112 may simultaneously communicate an electronic notification to the user device 118 of the user 116. The notification may indicate that a user is running in the area surrounding the pool 103.

In some implementations, the swimming pool 103 may be a large swimming pool that is open for public use. For example, a community center swimming pool. In these implementations, the one or more cameras may not be integrated with an in-home security system. Instead, the one or more cameras that are configured to monitor the area surrounding the swimming pool 103, may be in communication with a cloud processor. The cloud processor may be in communication with the notification system which is located at an area near the swimming pool 103. In these implementations, the notification system may be located at an area near a lifeguard booth. The notification system may indicate to the lifeguard the one or more zones of the surrounding pool area where user activity violates a pool rule. The notification system may include a user interface that list the rules associated with the usage of the public pool. For example, the notification system may include an LCD screen that lists the one or more rules. The one or more rules may include no eating, no diving into the shallow end of the pool, and no unattended children near the edge of the pool, and any other user set rule.

Figure 6:
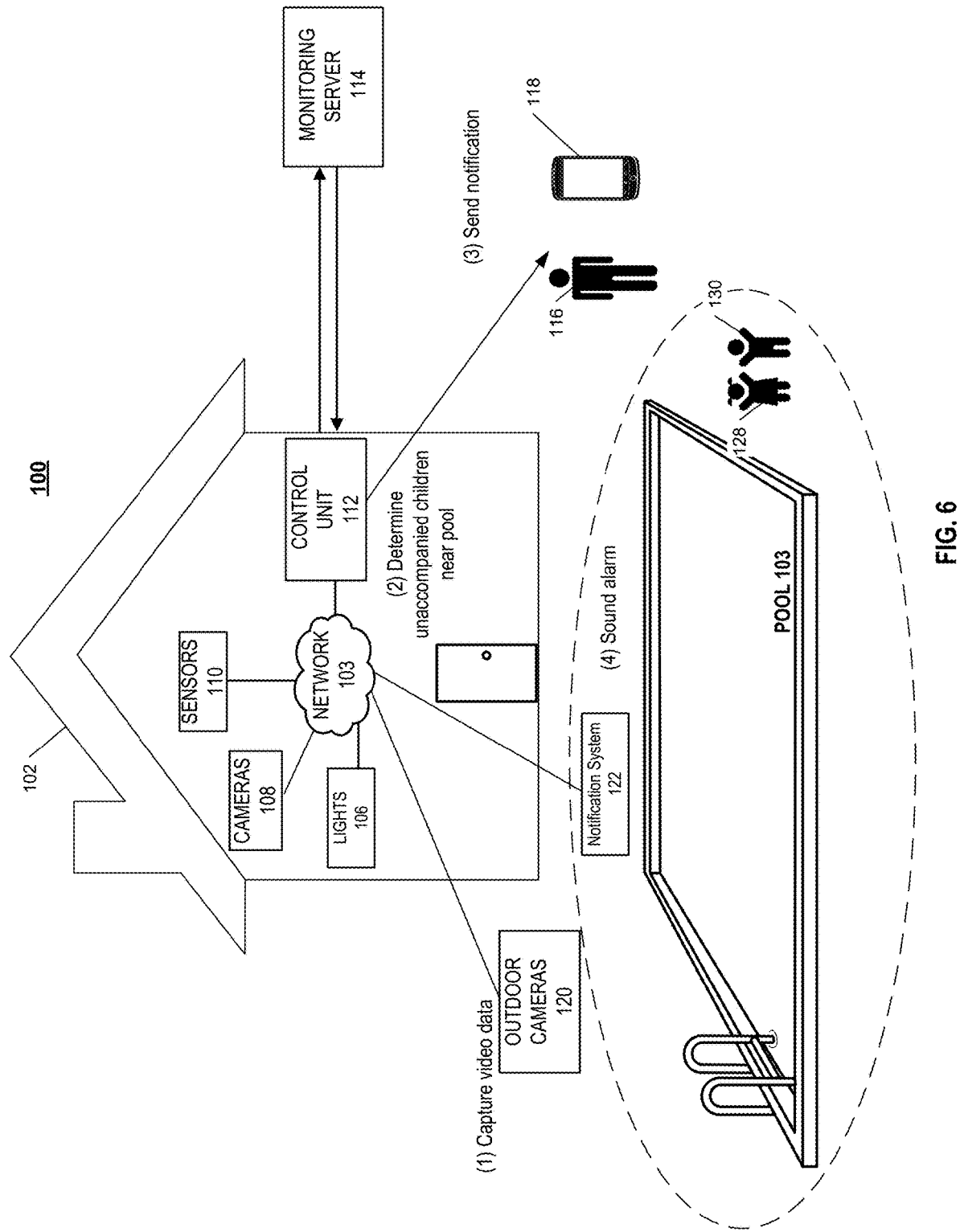
FIG. 6 illustrates an example system for detecting a child at the edge of the swimming pool.

As illustrated in FIG. 6, the one or more outdoor cameras 120 capture video data of the area surrounding the swimming pool 103. The one or more outdoor cameras 120 may be configured to detect when a person moves into the area surrounding the swimming pool 103, and may begin to capture video data when a person is detected. In some implementations, the one or more outdoor cameras 120 may be configured to continuously capture video data. The one or more outdoor cameras 120 communicate the video data to the monitor control unit 112. The monitor control unit 112 analyzes the video data to detect the activity of the one or more users in the area surrounding the swimming pool 103. The monitor control unit 112 may utilize one or more data processing techniques to determine the activity of the one or more users in the area surrounding the pool 103. The monitor control unit 112 may determine whether the user 124 is a child or an adult. For example, the user 116 may set a rule indicating that children should not be in the area surrounding the swimming pool 103 without being accompanied by an adult. Based on the user implementing this rule, the monitor control unit 112 may use one or more techniques to analyze the height and other physical characteristics of persons that enter the monitored area to determine whether the person is likely a child or an adult. In some implementations, the monitor control unit 112 may utilize a trained convolutional neural network (CNN) to classify users into an age class.

The resident user 116 may set a rule that no child should be unaccompanied by an adult when in a zone near the edge of the pool 103. Based on the user set rule, the monitor control unit 112 determines that each of the one or more users 128 and 130 detected near the edge of the pool 103 are children, and based on determining that each of the users around the pool 103 are children, communicates to the notification system to generate an alarm. The notification system may generate an audible alarm or a visual alarm to notify the residents of the property 102 that unaccompanied children are near the pool 103. The monitor control unit 112 simultaneously communicates an electronic notification to the user device 118 of an adult user 116 at the monitored property 102. In some implementations, the electronic notification may include one or more images of the children detected at the swimming pool 103. The user 116 may have the option to review the one or more images, and elect to end the alarm after reviewing the images. For example, the user 116 may end the alarm based on the children playing safely on the side of the pool 103.

Figure 7:
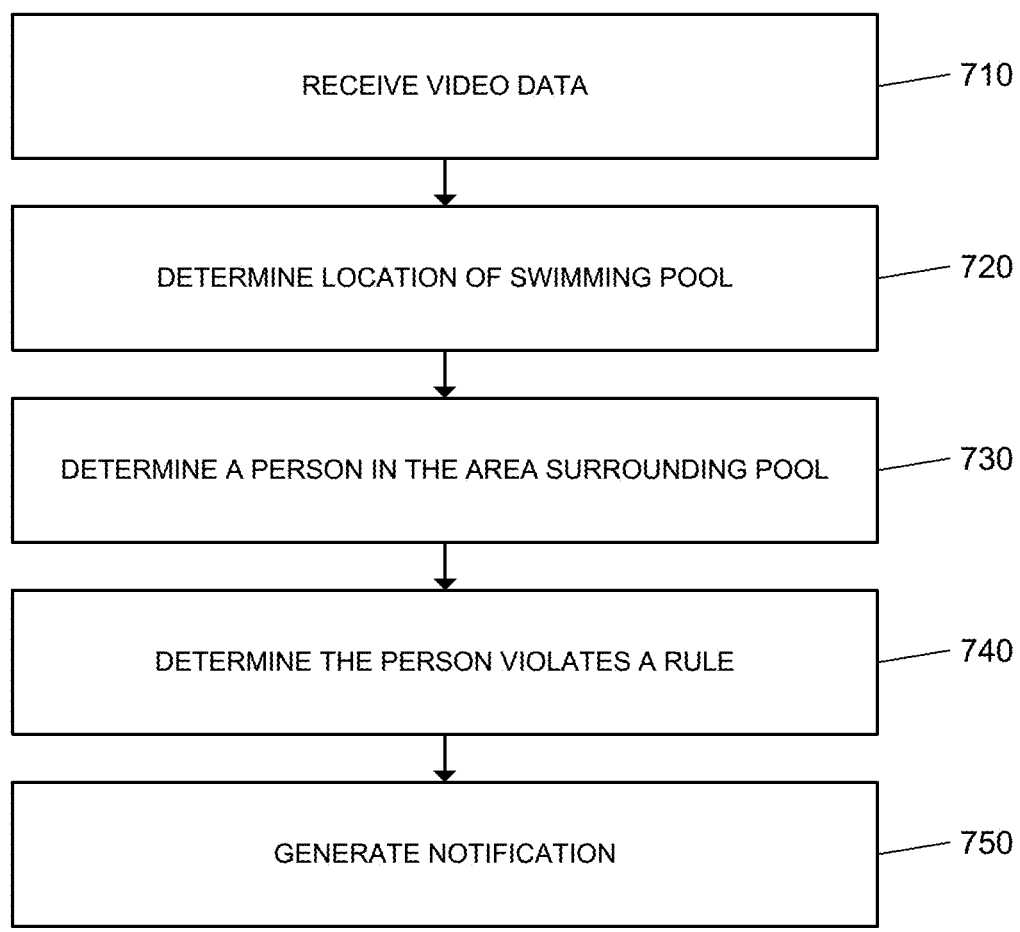
FIG. 7 is a flow chart of an example process for generating an alert.

FIG. 7 illustrates an example process 700 for generating a notification based on determining that a user violated a rule. The monitor control unit 112 receives video data (710). For example, the monitor control unit 112 receives video data from one or more cameras that monitor the swimming pool 103 and the surrounding area. The one or more cameras may be arranged so that the swimming pool 103 and the surrounding area are within the field of view of at least one of the camera. In some examples, the one or more cameras may be pan or tilt cameras that move to adjust their field of view. Each of the one or more cameras are time synchronized with each other and spatially calibrated against each other and the swimming pool 103. In some implementations, the one or more cameras that are configured to monitor the pool constantly capture video data and communicate the data to the monitor control unit 112. In other implementations, the one or more cameras initiate video data capture when a motion sensor detects motion.

The monitor control unit 112 determines the spatial location of the swimming pool (720). For example, the monitor control unit 112 analyzes the video data received from the one or more cameras to determine the spatial location of the swimming pool 103. The monitor control unit 112 may use one or more three-dimensional sensing technologies to identify the location of the swimming pool. The monitor control unit 112 may use one or more three-dimensional sensing technologies to identify the areas surrounding the swimming pool 103.

In some implementations, the one or more outdoor cameras may communicate the spatial characteristics sensed by the cameras to the monitor control unit 112, or may communicate the spatial characteristics sensed by the cameras to the one or more underwater pool sensors to improve the performance of the pool sensors. For example, the outdoor cameras may determine that the pool is a given size and shape, and this size and shape data may be used to create a rough model or set of parameters that may predict how sonar from the underwater sensor should behave.

The one or more outdoor cameras and the one or more underwater pool sensors are synchronization and spatial calibrated with each other. The synchronization and spatial calibration between the outdoor cameras and the underwater devices may be used to continuously track people and objects as they enter and exit the pool water. This association can provide gapless coverage of each person, ensuring that, for example, a child is always accounted for. Additionally, data about the person or object that might be easily determined by the outdoor cameras can be transferred to the underwater device or vice versa. For example, if someone jumps into the pool, the disturbance in the water might make it difficult for an underwater device to immediately determine if it is a person or an object. However, the outdoor camera has already been tracking the person as they approached the pool, and has already identified them as a person (perhaps even a specific person), and may communicate this data, as well as the location and trajectory that they are expected to enter the water, to the underwater camera. This data can then remain associated with the person or object as it is tracked by the underwater device and used to increase accuracy of that tracking. For example, an adult swimmer might be expected to move in different ways than a child, or a pool toy would.

The monitor control unit 112 determines that a person is in an area surrounding the swimming pool (730). For example, the monitor control unit determines that a person is in a first zone around the pool. The monitor control unit 112 analyzes the received video data to determine whether the video data includes video of a person, and determines which of a one or more user defined zones, the person is located. The user 116 may log into the monitoring application during the initial configuration to identify the one or more zones of the enforcement area. For example, the user 116 may identify one end of the pool as zone one, the middle portion as zone two, and the other end as zone three. In some examples, the user 116 may identify the zones based on the distance from the pool's edge. For example, zone one includes the area within two feet from the pool, zone two includes the area within four three to six feet from the pool.

The monitor control unit 112 may use facial analysis to detect the identity of the detected person. In examples where the swimming pool 103 is located at a monitored residence, the user 116 may register the one or more residents of the property during the configuration of the system. For example, the user 116 may provide one or more images of resident A, resident B, and child resident C through the monitoring application. When at least one camera detects a person around the swimming pool 103, the monitoring control unit 112 utilizes one or more facial analysis algorithms to determine whether the person is one of residents. For example, based on facial analysis the monitor control unit 112 determines that the person is resident A. The system tracks the resident A as the resident moves throughout the area surrounding the swimming pool 103. The system is configured to track each of the one or more users that enter the area surrounding the pool 113. The monitor control unit 112 may associate each user that enters the area surrounding the swimming pool 113 with a unique identifier. When the monitor control unit 112 analyzes additional video data, and determines that a user detected in the additional video data matches a known user, the monitor control unit 112 may track the activity or movements of the known user throughout the monitored area.

In examples where the swimming pool 103 is open to the public, the one or more cameras communicate the video data to a processor, the processor may use facial analysis to track the one or more users as they move through the monitored area around the swimming pool 103. For example, the processor determines an identity of a person and appends an identifier to the person, based on the identifier, the processor can track the one or more persons that are in the area surrounding the pool 103.

The monitor control unit 112 determines that the person within the area surrounding the pool violates a rule (740). For example, the monitoring control unit 112 determines that a person in zone three is eating. The monitor control unit 112 may utilize one or more deep learning techniques to identify the actions of the one or more persons within the monitored area. The monitoring control unit 112 may use a trained convolutional neural network (CNN) to analyze the captured video data to determine the actions of the person in the captured video. The convolutional neural network may be trained to identify human actions such as, eating, drinking, running, and diving into the pool. In some examples, the convolutional neural network may be trained to classify a person into an age class, this classification may be used to determine whether the person is an adult or is a child. The convolutional neural network may be trained to identify objects such as food and drink, or to identify harmful objects such as a knife, scissors, or a weapon. A deep neural network (DNN) The convolutional neural network may be trained to identify when a user is about to dive into the swimming pool 103.

The monitor control unit 112 determines the action of the person and determines whether the action violates a rule based on comparing to the one or more user set rules. For example, the monitor control unit 112 determines that a person is drinking in a zone where drinking is prohibited. In examples where the person is identified as a child resident of the property, the monitor control unit 112 may determine that a rule is violated when the child is detected in the area surrounding the swimming pool 103, and the video data does not indicate the presence of another adult in the area surrounding the pool 103. In some examples, the user 116 may set a rule that prohibits running in a first zone closest to the pool 103, but allows running in a second zone. In such an example, when a person is determined to be running in the second zone, and moves into the first zone, the monitor control unit 112 determines that the person violated a rule.

The user may set a rule that users may not be engaged in boisterous play or roughhousing in the area surrounding the pool 103. The monitor control unit 112 may be configured to detect the behavior of the users in the monitored area based on heuristics of their motion. The user may set a rule that there can be no climbing in particular areas around the swimming pool 103. The monitor control unit 112 may be configured to use human tracking techniques to detect when a user is climbing in a zone that restricts users from climbing.

In some implementations, the monitor control unit 112 may be configured to detect pets and other animals that enter the monitored area around the swimming pool 103. For example, the resident user may set a rule that indicates that pets are not allowed within the monitored area around the pool. In some implementations the user may set a rule that items such as knives, or other dangerous items should not be brought into the monitored area. In these implementations, the user may set a list of prohibited items, and the monitor control unit 112 may be trained to identify the one or more prohibited items.

The notification system generates a notification (750). For example, the notification system 122 may generate an audible alarm when a child is detected close to the edge of the swimming pool 103. The user 116 may specify the type of notification that is generated based on the user set rule that is violated. For example, the user 116 may specify that the notification system generate a whistle sound when a person is detected as running in the area surrounding the pool 103. On the other hand, the user 116 may specify that the notification system generate a flashing light visual alarm and send a notification to the user device 118 of the user 116 when the system determines that a person is likely attempting to dive into a shallow end of the pool 103. The user 116 may specify that the notifications are escalated when the person detected of violating a rule is a repeat offender, or does not cease their behavior.

In some examples, the notification system 122 may be used to remind each of a one or more tracked users to perform one or more actions. For example, the notification system may be used to send a notification to the user device of a user A, when the system determines that user A has not been detected as applying sunblock in the past hour. For another example, the notification system may be used to send a notification to the user device of a user B, when the system determines that user B consumed more than three beers and should not enter the swimming pool. In some examples, the notification system may generate a voice warning to indicate to the adult user that they have consumed their limit of beers. For another example, the notification system may be used to send a notification to a user when the system determines that the user has been at the pool for over three hours.

In some implementations, where the swimming pool is a public pool, the notification system 122 may serve as an aid to a lifeguard. In these implementations, the notification system may be an LCD user interface that identifies the zone where the violation occurred. The user interface may include the violation information overlaid on an actual or synthesized video feed of the pool area, or an abstract graphical representation of the pool as an overhead plan or other perspective. The display could be optimized for a handheld device, lifeguard tower mounted display, publicly visible monitor. Based on the information received from the notification system 122, the lifeguard may turn his or her attention to the area where the violation occurred. In some implementations, the notification system may output voice commands that indicate the current weather conditions, such as temperature, to the one or more users at the swimming pool 103. In some implementations, the system may automate pool or walkway lighting, blinking or changing colors to indicate the location and/or severity of the violation.

Figure 8:
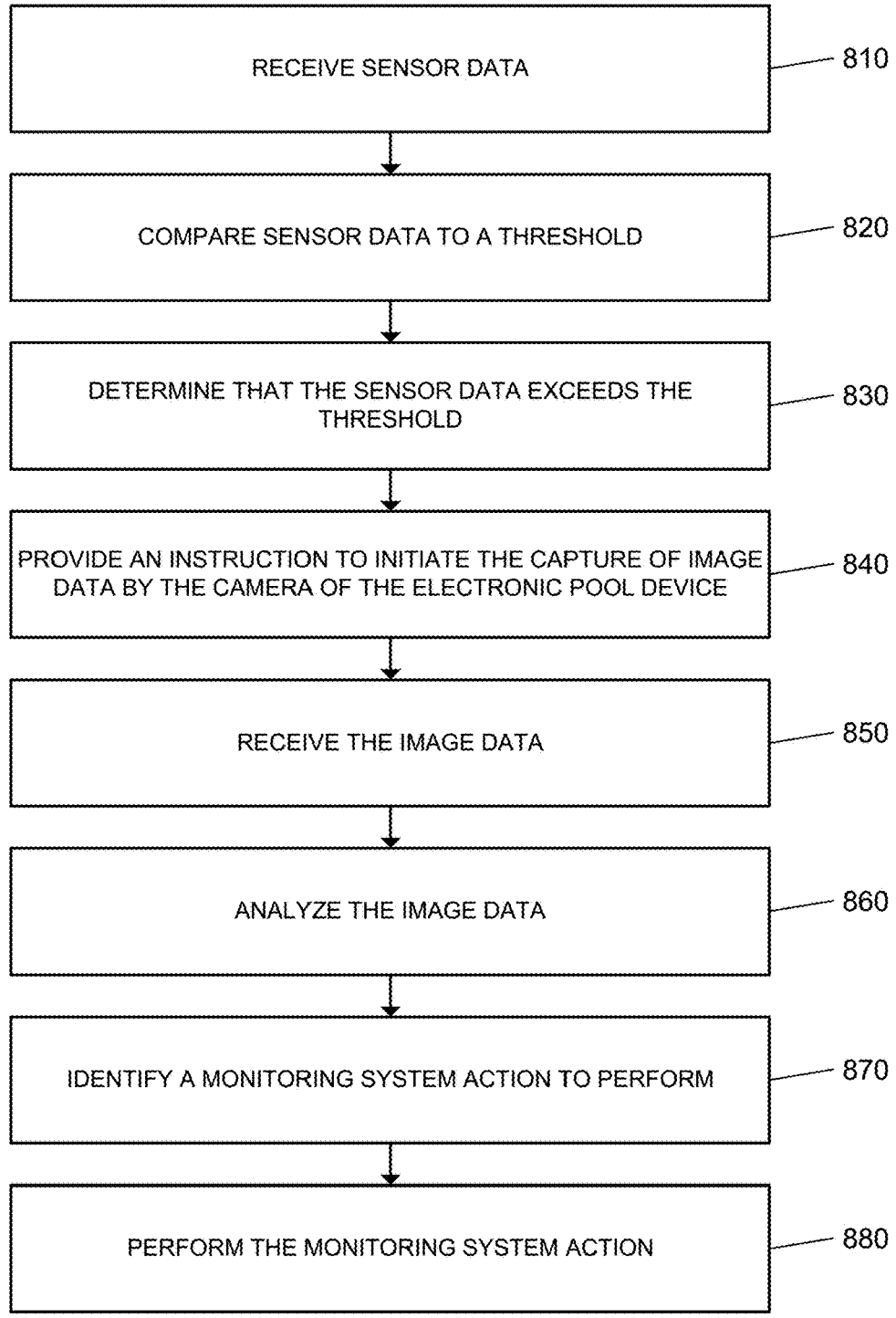
FIG. 8 is a flow chart of an example process for performing a monitoring system action.

FIG. 8 illustrates an example process 800 for performing an action. The process 800 may be performed by a monitoring system at a property 102 with an electronic pool device 104 that is configured to monitor a swimming pool 103 at the property 102. For example, the process 800 may be performed by the control unit 112 that is in communication with the electronic pool device 104 and one or more other sensors located throughout the monitored property 102.

The process 800 includes receiving sensor data (810). For example, the control unit 112 may receive motion sensor data from a motion sensor on the camera portion of an electronic pool device 104. The electronic pool device 104 is configured to monitor the conditions of the swimming pool at the property 102.

In some implementations, the camera portion of the electronic pool device is waterproof and is located under a surface of water in the swimming pool 1003 and the surface portion of the electronic pool device 104 is located above the surface of water in the swimming pool 103, and is configured to include an antenna and a microphone, where the one or more sensors included in the surface portion of the electronic pool device 104 include one or more motion detecting sensors. For example, the electronic pool device 104 includes a camera portion that is configured to be placed under the surface of the water, and a surface portion that includes one or more motion detecting sensors.

The one or more motion detecting sensors may include an accelerometer, a gyroscope, a mercury switch, or any other appropriate motion detecting sensors. The one or more motion sensors are configured to detect motion caused when an object enters the swimming pool, that is, the motion caused when an object breaks the surface of the water in the swimming pool 103.

In some implementations, the camera portion of the electronic pool device 104 includes a pH monitor that is configured to measure the pH of the water in the swimming pool 103. In these implementations, the control unit 112 may receive pH sensor data from the pH monitor of the electronic pool device 104. The camera portion of the electronic pool device 104 may include a thermometer that is configured to measure the temperature of the swimming pool water. In these implementations, a resident of the property 102 may set one or more preferences for receiving notifications from the control unit 112 based on the measured pH readings and the measured water temperature.

The process 800 includes comparing the sensor data to a threshold (820). For example, the control unit 112 compares the motion sensor data to a motion sensor threshold. In some implementations, the process includes receiving, from the electronic pool device 104, the sensor data by receiving, from a motion sensor in the surface portion of the electronic pool device 104, motion sensor data, receiving, from an external server, weather data, and based on receiving the weather data, determining a motion threshold. For example, the motion threshold may be a motion threshold that is determined by the control unit 112 based on the local weather conditions at the monitored property 102.

In some implementations, the control unit 112 at the monitored property 102 may receive weather data from a weather data server 124. The weather data server 124 may be in direct communication with the control unit 112, or the weather data server 124 may communicate with a monitoring server 114 which in turn communicates with the control unit 112. The control unit 112 may adjust the motion threshold based on the weather data indicating windy or rainy conditions.

In some implementations, the control unit 112 may adjust the motion threshold based on the armed status of the monitoring system at the property 102. For example, when the monitoring system at the monitored property 102 is armed away, the system assumes that the residents of the property 102 are away from the property 102, and the control unit 112 increases the motion threshold. For another example, when the monitoring system is armed stay, the system assumes that the residents of the property are at the property, and the control unit 112 decreases the motion threshold.

The process 800 involves determining that the sensor data exceeds the threshold based on comparing the sensor data to a threshold (830). For example, the control unit 112 determines that the motion sensor data exceeds the motion threshold. For another example, the control unit 12 determines that the pH sensor data exceeds the pH threshold.

The process 800 involves providing an instruction to initiate the capture of image data by the camera of the electronic pool device (840). For example, the control unit 112 prompts the camera of the electronic pool device 104 to capture image data. In some implementations, the electronic pool device 104 is placed in the swimming pool 103 when the pool is not being utilized. In these implementations, any motion that is detected by the one or more motion sensors in the surface portion of the electronic pool device 104 may be considered unexpected motion. When the control unit 112 detects unexpected motion that exceeds the motion threshold, the control unit 112 sends a command to the camera of the electronic pool device 104 to capture image data to determine the cause of the unexpected motion.

The process 800 involves receiving the image data from the camera of the electronic pool device (850). For example, the control unit 112 receives the captured image data via Bluetooth, Z-Wave, ZigBee, Wi-Fi, or other suitable form of wireless communication, from the electronic pool device.

The process 800 involves analyzing the image data received from the camera of the electronic pool device (860). For example, the control unit 112 utilizes one or more image analytic techniques to analyze the received images to determine whether the motion was caused by a person or an object. In some implementations, when the control unit 112 determines that the motion was caused by a person, the control unit 112 may perform facial recognition on the image data to identify the person detected in the swimming pool 103. The resident user may select an option to have the control unit 112 generate an alarm based on determining that the motion was caused by a person that is determined to be a trespasser.

The process 800 involves identifying a monitoring system action to perform based on analyzing the image data (870). For example, the control unit 112 determines to generate an audible alarm at the monitored property 102 based on determining that the motion in the swimming pool 103 was caused by a person when the swimming pool 103 should not be in use. In some implementations, when the electronic pool device 104 is placed in the swimming pool 103 when the pool 103 is not in use, the control unit 112 determines that any motion in the swimming pool 103 is unexpected motion. When the unexpected motion is detected in the swimming pool 103, the control unit 112 analyzes the received image data to determine whether the motion was caused by a person or an object. The control unit 112 may determine to generate an audible alarm at the monitored property 102 based on determining that the motion in the swimming pool 103 was caused by a person.

In some examples, the control unit 112 may determine to switch on one or more lights in the vicinity of the swimming pool 103 based on determining that the motion in the swimming pool 103 was caused by person. In other examples, the control unit 112 may determine to generate at audible alarm at the property 102 based on determining that the motion in the swimming pool 103 was caused by a person. In yet another example, the control unit 112 may determine not to generate a notification based on determining that the motion in the swimming pool 103 was caused by an object. For example, when the control unit 112 analyzes the image data to determine that the motion in the swimming pool 103 was caused by a tree branch, the control unit 112 determines that a notification does not need to be communicated to the user device of the resident of the property 102.

The process 800 involves performing the monitoring system action (880). For example, the control unit 112 performs a monitoring system action by communicating a notification to a user device of a resident of the property 102 indicating that the motion in the swimming pool 103 was caused by a person.

In some implementations, the electronic pool device 104 includes a sonar detector. In these implementations, the camera portion of the electronic pool device 104 may include a sonar detector that is configured to detect objects under the surface of the water in the swimming pool 103. In these implementations, the electronic pool device 104 may be configured to remain in the swimming pool 103 at all times.

The sonar detector is configured to characterize the underwater portion of the empty swimming pool 103 during the configuration of the electronic pool device 104. The sonar detector is configured to emit sound pulses and to detect the sound pulses that are reflected off the side surfaces of the swimming pool 103, and back to the sonar detector. Based on this, the sonar detector generates a signature reflection pattern of the swimming pool 103.

The sonar detector is configured to detect when there is a change in the reflection pattern of the underwater profile of the pool 103, based on the reflection data received at the detector. When the sonar detector receives a reflection pattern that is different than the signature reflection pattern collected during configuration, the sonar detector determines an object entered the swimming pool 103. The electronic pool device 104 communicates the sonar data to the control unit 112. The control unit 112 may implement one or more algorithms to determine whether the data detected by the sonar detector was caused by an object and not by other factors such as, weather or a vibration from the pool pump.

The control unit 112 may be configured to receive image data from the camera of the electronic pool device 104 and from the one or more cameras located in the vicinity of the swimming pool 103. In some implementations, the control unit 112 may be configured to receive image data from one or more underwater cameras that are in communicating with each other and in communication with the electronic pool device 104. In these implementations, the control unit 112 may be configured to monitor the activity around the swimming pool 103. The monitor control unit 112 may utilize video analytics and other techniques to determine when a user is performing a prohibited action in the area surrounding the swimming pool 103. In these implementations, the resident user 116, may set one or more rules that are applicable to one or more user zones around the swimming pool 103 through a monitoring application on the user device.

As describes above with reference to FIG. 5, the user 116 may customize the rules and the notifications generated when a user violates the rules. For example, the resident user 116 may input a rule that the control unit sounds an audible alarm at the property 102 when a child enters the swimming pool 103 without being supervised by an adult. The control unit 112 may determine whether a person by the swimming pool 103 is a child or an adult by using one or more techniques to analyze the height and other physical characteristics of persons that enter the monitored area.

In some implementations, the monitor control unit 112 may utilize a trained convolutional neural network (CNN) to classify users into an age class. When the control unit 112 determines that a user in the vicinity of the pool 103 is a child, and subsequently determines that the user entered the swimming pool 103, and is not supervised by an adult, the control unit sounds an audible alarm at the monitored property 102. In some examples, the control unit 112 may communicate a notification to the user device of the resident of the property 102 indicating that an unsupervised child entered the swimming pool 103. In some examples, the notification may include the captured image data. In these examples, the resident user may have the option to review the one or more images, and elect to end the alarm after reviewing the images. For example, the user 116 may end the alarm based on determining that the child is wearing a floatation device.

The one or more outdoor cameras 120 may be time-synchronized and spatially calibrated with each other and the spatial dimensions of the swimming pool 103. The one or more cameras 120 may be configured to track a user as the user moves around in the area surrounding the swimming pool 103. The one or more cameras may use facial analysis and other techniques to track one or more different users as the one or more users move around in the area surrounding the swimming pool 103. The one or more cameras 120 may use identifiers to tag the one or more users as the users navigate within the monitored area. The monitor control unit 112 may use one or more video analytics techniques to detect the activity of the user 126. For example, the monitor control unit 112 utilizes one or more deep learning techniques and or three-dimensional sensing technologies to determine the location of a user with respect to the swimming pool 103, and to determine the activity of the user while in the monitored area.

In some implementations, the monitoring system includes one or more cameras located in a vicinity of the pool, where each of the one or more cameras are configured to capture image data of an area surrounding the pool. The monitor control unit 112 may be configured to receive, from a user, a condition and an action to perform based on the condition being met. For example, the user may be an administrative user at a public swimming pool, and the administrative user may identify one or more rules that indicate actions that are prohibited in the vicinity of the swimming pool.

The monitor control unit 112 may receive, from the one or more cameras located in the vicinity of the pool, additional image data, and may be configured to analyze the additional image data using one or more image analytic techniques. For example, the monitor control unit 112 may be configured to use one or more deep learning techniques to identify a person in the image data, and to determine an action of the person in the identified image data. For another example, the monitor control unit 112 may be configured to use a trained convolutional neural network (CNN) to analyze the additional image data.

The monitor control unit 112 may be configured to determine that a condition has been met based on analyzing the additional image data using the one or more image analytic techniques. The monitor control unit 112 may be configured to perform the action based on determining that a condition has been met. For example, the monitor control unit 112 may be configured to generate an audible output to notify a person that alcoholic beverages are not allowed in the vicinity of the pool. For another example, the monitor control unit 112 may be configured to generate a whistle sound that mimics the whistle sound of a lifeguard based on determining that a person is running in the vicinity of pool. For another example, the monitor control unit 112 may be configured to generate an audible alarm based on determining that a pet is in the vicinity of the pool.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

The invention claimed is:

1. A monitoring system that is configured to monitor a property, the monitoring system comprising:
   an electronic pool device that is configured to monitor a swimming pool located at the property, the electronic pool device including a camera portion with a camera that is configured to capture image data, and a surface portion that includes one or more sensors that are configured to generate sensor data; and
   a monitor control unit that is configured to:
   receive, from the electronic pool device, the sensor data;
   compare the sensor data to a threshold;
   based on comparing the sensor data to a threshold, determine that the sensor data exceeds the threshold;
   based on determining that the sensor data exceeds the threshold, provide an instruction to initiate the capture of image data by the camera of the electronic pool device;
   receive, from the camera of the electronic pool device, the image data;

analyze the image data;
based on analyzing the image data, identify a monitoring system action to perform; and
perform the monitoring system action.

2. The system of claim 1, wherein:
the camera portion of the electronic pool device is waterproof and is located under a surface of water in the swimming pool; and
the surface portion of the electronic pool device is located above the surface of water in the swimming pool, and is configured to include an antenna and a microphone, wherein the one or more sensors included in the surface portion of the electronic pool device include one or more motion detecting sensors.

3. The system of claim 2, wherein:
the one or more motion detecting sensors include at least one of an accelerometer, a gyroscope, or a mercury switch.

4. The system of claim 3, wherein, the monitor control unit is configured to:
determine that motion of a surface of the pool detected by a motion detector sensor indicates that an object has entered the pool; and
in response to determining that motion of a surface of the pool detected by the motion detector sensor indicates that an object has entered the pool, capture an image of the pool by an underwater camera.

5. The system of claim 1, wherein the monitor control unit is configured to:
receive, from the electronic pool device, the sensor data by receiving motion sensor data;
compare the sensor data to a threshold by comparing the motion sensor data to a motion data threshold;
based on comparing the motion sensor data to a motion data threshold, determine that the motion sensor data exceeds the motion threshold;
analyze the image data using one or more image analytic techniques;
based on analyzing the image data using the one or more image analytic techniques, identifying a monitoring system action to perform by determining whether the motion was caused by an object or a person; and
based on determining that the motion was caused by a person, performing the monitoring system action by communicating a notification to the use device of a resident of the property.

6. The system of claim 1, wherein the monitor control unit is configured to:
receive, from the electronic pool device, the sensor data by receiving motion sensor data;
compare the sensor data to a threshold by comparing the motion sensor data to a motion threshold;
based on comparing the motion sensor data to a motion threshold, determine that the motion sensor data exceeds the motion threshold;
analyze the image data using one or more video analytic techniques;
based on analyzing the image data using the one or more video analytic techniques, identifying a monitoring system action to perform by determining whether the motion was caused by an object or a person; and
based on determining that the motion was caused by an object, performing the monitoring system action by not sounding an audible alarm at the property.

7. The system of claim 1, wherein the monitor control unit is configured to:
receive, from the electronic pool device, the sensor data by receiving, from a motion sensor in the surface portion of the electronic pool device, motion sensor data;
receive, from an external server, weather data; and
based on receiving the weather data, determine a motion threshold.

8. The system of claim 7, wherein the monitor control unit is configured to:
determine an armed status of the monitoring system is armed away;
based on determining an armed status of the monitoring system is armed away, increase the motion threshold; and
compare the motion sensor data to the increased motion threshold.

9. The system of claim 7, wherein the monitor control unit is configured to:
determine an armed status of the monitoring system is unarmed;
based on determining an armed status of the monitoring system is unarmed, decrease the motion threshold; and
compare the motion sensor data to the decreased motion threshold.

10. The system of claim 1, wherein the monitor control unit is configured to:
receive, from the electronic pool device, the sensor data by receiving, from a pH sensor in the camera portion of the electronic pool device, pH data, wherein the pH sensor is configured to measure a pH of water in the swimming pool;
compare the pH data to a pH threshold;
based on comparing the pH data to a pH threshold, determine that the pH data exceeds the pH threshold; and
based on determining that the pH data exceeds the pH threshold, perform a monitoring system action by communicating a notification to a user device of the resident of the property.

11. The system of claim 1, wherein:
the monitoring system further comprises:
one or more cameras located in a vicinity of the pool, wherein each of the one or more cameras are configured to capture image data of an area surrounding the pool; and
the monitor control unit is further configured to:
receive, from a user, a condition and an action to perform based on the condition being met;
receive, from the one or more cameras located in the vicinity of the pool, additional image data;
analyze the additional image data using one or more image analytic techniques;
based on analyzing the additional image data using the one or more image analytic techniques, determine that a condition has been met; and
based on determining that a condition has been met, perform the action.

12. The system of claim 11, wherein the monitor control unit is configured to:
analyze the additional image data using one or more image analytic techniques by, analyzing the additional image data using one or more deep learning techniques to (i) identify a person in the image data, and (ii) determine an action of the person identified in the image data.

13. The system of claim 12, wherein the monitor control unit is configured to:

analyze the additional image data using one or more image analytic techniques by, analyzing the additional image data using a trained convolutional neural network (CNN).

14. The system of claim 12, wherein the monitor control unit is configured to:
   determine that a condition has been met by determining that a person is drinking an alcoholic beverage in the vicinity of the pool; and
   based on determining that the condition has been met, perform the action by generating an audible output to notify the person that alcoholic beverages are not allowed.

15. The system of claim 12, wherein the monitor control unit is configured to:
   determine that a condition has been met by determining that a person is running in the vicinity of the pool; and
   based on determining that the condition has been met, perform the action by generating a whistle sound to mimic a whistle sound of a lifeguard.

16. The system of claim 11, wherein the monitor control unit is configured to:
   determine that a condition has been met by determining that a pet is in the vicinity of the pool; and
   based on determining that the condition has been met, perform the action by generating an audible alarm.

17. The system of claim 12, wherein the monitor control unit is configured to:
   receive, from the user, the condition and the action to perform based on the condition being met by, receiving, from an administrative user at a public swimming pool, a rule that indicates an activity that is prohibited the vicinity of the pool, and an alert to generate based on determining the activity occurred in the vicinity of the pool.

18. A monitoring system that is configured to monitor a property, the monitor system comprising:
   an electronic pool device that is configured to monitor a swimming pool located at the property, the electronic pool device including a sonar detector in a camera portion of the electronic pool device;
   one or more cameras located in a vicinity of the pool, wherein each of the one or more cameras are configured to capture image data; and
   a monitor control unit that is configured to:
      receive, from the one or more cameras located in the vicinity of the pool, image data;
      receive, from the sonar detector in the camera portion of the electronic pool device, sonar data;
      analyze the image data;
      analyze the sonar data;
      based on analyzing the image data and the sonar data, determine that a child entered the swimming pool unsupervised; and
      based on determining that the child entered the swimming pool unsupervised, perform a monitoring system action by sounding an audible alarm at the monitored property.

19. The monitoring system of claim 18, wherein the monitor control unit is configured to:
   perform a monitoring system action by, communicating a notification to the user device of a resident of the property.

20. The monitoring system of claim 18, wherein the monitor control unit is configured to:
   analyze the sonar data by comparing the received sonar data to a sonar reflection pattern of the swimming pool.

* * * * *